United States Patent [19]

Degrave et al.

[11] Patent Number: 4,633,169
[45] Date of Patent: Dec. 30, 1986

[54] BLOOD PARTICLE ANALYZER

[75] Inventors: Philippe L. Degrave, Viroflay; Jean P. Lepage, Margny les Compiègnes, both of France

[73] Assignee: Kontron Holding AG, Zurich, Switzerland

[21] Appl. No.: 625,754

[22] Filed: Jun. 28, 1984

[30] Foreign Application Priority Data

Jul. 8, 1983 [CH] Switzerland .................. 3769/83

[51] Int. Cl.⁴ .................................. G01N 27/02
[52] U.S. Cl. ............................. 324/71.1; 324/77 A
[58] Field of Search ............ 324/71.1, 71.4, 77 D, 324/77 A, 782; 377/10, 11, 12; 364/555

[56] References Cited

U.S. PATENT DOCUMENTS

| | | | |
|---|---|---|---|
| 2,656,508 | 10/1953 | Coulter | 324/71.1 |
| 3,733,547 | 5/1973 | Coulter et al. | 324/71.1 |
| 3,733,548 | 5/1973 | Coulter et al. | 324/71.1 |
| 3,801,903 | 4/1974 | Hogg | 324/71.1 |
| 3,801,904 | 4/1974 | Hogg et al. | 324/71.1 |
| 3,820,019 | 6/1974 | Doty et al. | 324/71.1 |
| 3,820,020 | 6/1974 | Doty et al. | 324/71.1 |
| 3,961,249 | 6/1976 | Coulter | 324/71.1 |

FOREIGN PATENT DOCUMENTS

| | | |
|---|---|---|
| 2539864 | 3/1977 | Fed. Rep. of Germany . |
| 2116601 | 7/1972 | France . |
| 2146819 | 3/1973 | France . |
| 1394182 | 5/1975 | United Kingdom . |

OTHER PUBLICATIONS

Lepage, J. P., "Realisation D'Une Chaine D'Analyse Pour Construire en Temps Reel les Spectres Detailles Des Particules DuSang", report to Laboratoire de Développment, Roche Bioelectronique Kontron, France.

Roche Bioelectronique Kontron, "Electronique d'Acquisition et de Visualisation", report to Comissariat A l'Energie, Sarclay, France.

Schulz et al., Medical and Biological Engineering, vol. II, No. 4, pp. 447-454 (Jul. 1973).

Primary Examiner—Stewart J. Levy
Assistant Examiner—Kevin D. O'Shea
Attorney, Agent, or Firm—Jon S. Saxe; Bernard S. Leon; George W. Johnston

[57] ABSTRACT

A method for the analysis of particles in suspension in a fluid having a conductivity different from that of the particles, in particular a method for the analysis of blood particles is disclosed. The method includes the following steps: passing the fluid through an orifice, applying an electronic signal across the orifice, and producing electronic pulses corresponding to the changes in the signal level caused by the passage of the particles through the orifice. The invention is also concerned with a device for carrying out the method.

6 Claims, 10 Drawing Figures

BLOOD PARTICLE ANALYZER

BACKGROUND

1. Field of the Invention

The invention concerns a device and method for analyzing particles suspended in a solution. This invention relates, in particular, to the discrimination of noise signals in an electronic device for the analysis of particles by means of which particulate systems can be studied according to the Coulter detection principle. The invention especially applies to blood analysis.

2. Description

The Coulter detection principle is described in U.S. Pat. No. 2,656,508. According to this principle, a liquid electrolyte containing particles in suspension is passed from a first container to a second container through a microscopic passage or orifice arranged in an insulating wall, the orifice being placed in an electrical field formed by the application of electrical energy to electrodes immersed in the electrolyte and placed on either side of the orifice, such that when a microscopic particle in suspension in the electrolyte passes through the orifice a momentary variation in the electrical impedance of the electrolyte measured between the electrodes is produced. This variation in impedance derives part of the excitation energy in the associated electrical measuring circuits and produces an electrical pulse in these circuits. On condition that the path of the particle coincides approximately with the longitudinal axis of the orifice, the amplitude of this pulse is a fairly accurate indication of the volume of the particle. Counting the pulses produced permits a counting of the particles that pass through the orifice up to frequencies of several thousand per second.

In principle, in a particle counter functioning according to the Coulter principle, each pulse is counted, its amplitude is recorded, and the whole of the information obtained in this way is presented in the form of a histogram, which shows the distribution of particles according to their volume. In a device for the analysis of blood particles a certain number of parameters that are important for medical diagnostics (e.g. the hematocrit value) are calculated from the information contained in such a histogram. It is therefore important that this information should be as accurate as possible. If all of the pulses generated by the Coulter principle are considered, the histogram contains partly erroneous information, because among the pulses generated there are on the one hand electrical noise signals and on the other hand pulses corresponding to the passage of particles the trajectory of which is clearly away from the longitudinal axis of the orifice. The amplitude of the latter type of pulse is not representative of the volume of the corresponding particles.

A relatively long orifice could be used in order to reduce the number of the latter type of pulses. However, this has two major disadvantages: on the one hand such an orifice becomes blocked up more frequently and on the other hand counting errors occur much more frequently due to the fact that particles which appear simultaneously in the orifice are incorrectly counted as a single particle. In order to avoid these disadvantages it is therefore advantageous to use an orifice of relatively short length, i.e. a length equal to or less than its diameter.

With regard to the noise signals which in practical applications accompany the pulses generated by the Coulter principle it is interesting to note that it is rather difficult to detect them and to separate them from the useful pulses, as among the useful pulses there are pulses of amplitude comparable with certain noise signals. In addition, noise often affects the edges of particle pulses and thus impedes their discrimination by means of amplitude thresholds. In order to solve this problem it has already been proposed to eliminate all pulses of which the rise time is less than a reference value (French Patent published under No. 2,146,819). Nevertheless, the continuously growing need for greater accuracy and a diversified commercial use of particle analyser devices has led to the conclusion that the discrimination of noise signals must be improved.

SUMMARY OF THE INVENTION

The present invention concerns a method and device for the analysis of particles using the Coulter detection principle, according to which for the passage of each particle through a measuring orifice a corresponding electrical pulse is produced.

In order to discriminate pulses corresponding to particles which cross the orifice along a trajectory away from the axis, one aspect of the method provides the following steps: producing a first auxiliary signal the waveform of which corresponds to the first derivative with respect to time of the waveform of each pulse; detecting a first instant ($t_1$) at which the amplitude of the first auxiliary signal exceeds a predetermined first threshold level ($S_1$); checking at a second instant ($t_2$), which follows at a predetermined time interval (To) after the first instant ($t_1$) whether the amplitude of the first auxiliary signal at the said second instant has already exceeded a second predetermined threshold level ($S_2$), which is greater than the first threshold level; and if the said amplitude has exceeded the second predetermined threshold level ($S_2$), which is greater than the first threshold level and if the said amplitude has exceeded the second threshold level ($S_2$), considering the pulse as a pulse (A) of zero amplitude.

In order to reject noise signals which would otherwise be treated as valid pulses, another aspect of the method provides the following steps: producing a first auxiliary signal the waveform of which corresponds to the first derivative with respect to time of the waveform of each pulse; comparing the time interval ($\tau$) contained between a third instant ($t_3$), defined by the point of zero slope at the peak of the pulse, and a fourth instant ($t_4$), defined by the point in the first auxiliary signal which corresponds with the end of the falling edge of the pulse and where the first auxiliary signal reaches zero value, with a predetermined threhold duration ($T_1$); if the measured interval ($\tau$) is shorter than the threshold duration ($T_1$), not counting the pulse and not taking the information given by that pulse into consideration, or if the measured interval ($\tau$) is equal to or longer than the threshold duration ($T_1$), considering the pulse as being representative of a particle and taking account of the information given by that pulse.

DETAILED DESCRIPTION OF THE INVENTION

The invention is concerned with a method for the analysis of particles in suspension in a fluid having a conductivity different from that of the particles, in particular a method for the analysis of blood particles, including the following steps: passing the fluid through an orifice, applying an electronic signal across the orifice, and producing electronic pulses corresponding to the changes in the signal level caused by the passage of the particles through the orifice. The invention is also concerned with a device for carrying out the method.

The present invention provides an economical solution to the problems indicated above while permitting operation with a relatively short orifice. A first part of this solution to the problem consists in discriminating the pulses corresponding to the passages of particles, the trajectories of which are away from the axis of the orifice. A second part of this solution to the problem consists in rejecting noise pulses, which obviously do not correspond with the passage of particles through the orifice.

According to the invention, the first part of the problem indicated above is solved by a method of the type mentioned in the first paragraph of this description, which includes the following additional steps:

producing a first auxiliary signal the waveform of which corresponds to the first derivative with respect to time of the waveform of each pulse, detecting a first instant at which the amplitude of the first auxiliary signal exceeds a predetermined first threshold level, checking at a second instant, which follows at a predetermined time interval after the first instant, whether the amplitude of the first auxiliary signal at the said second instant has already exceeded a second predetermined threshold level, which is greater than the first threshold level, and if the said amplitude has exceeded the second threshold level, considering the pulse as a pulse of zero amplitude.

In order to carry out this method the invention provides a device containing a pulse detector which includes the following circuits:

A differentiation circuit to produce the first auxiliary signal the waveform of which corresponds to the first derivative with respect to time of the wave form of each pulse, a first comparator connected to the output of the differentation circuit to detect a first instant at which the first auxiliary signal exceeds a predetermined first threshold level and to supply a corresponding output signal, a counter connected to the output of the first comparator to produce as an output signal a pulse the duration of which defines a predetermined time interval starting from the said first instant, a second comparator connected to the output of the differentiation circuit to detect a second instant at which the first auxiliary signal exceeds a second predetermined threshold level, which is larger than the first threshold level, and to provide a corresponding output signal, and a logical circuit connected to the outputs of the first and second comparators and of the counter, and intended to control the consideration of pulses received at the input of the differentiation circuit as pulses of zero amplitude if the second instant falls within the time interval defined by the counter.

According to the invention, the second part of the problem indicated above is solved by a method of the type mentioned in the first paragraph of this description, which includes the following additional steps:

Producing a first auxiliary signal the waveform of which corresponds to the first derivative with respect to time of the waveform of each pulse, comparing the time interval between a third instant, defined by the point of zero slope at the peak of the pulse, and a fourth instant, defined by the point in the first auxiliary signal which corresponds with the end of the falling edge of the pulse and where the first auxiliary signal reaches zero value, with a predetermined threshold duration, if the measured interval is shorter than the threshold duration, not counting the pulse and not taking the information given by that pulse into consideration, or if the measured interval is equal to or longer than the threshold duration, considering the pulse as being representative of a particle and taking account of the information given by that pulse.

For the implementation of the latter method the invention provides a device containing a pulse detector which includes the following circuits:

A differentiation circuit to produce the first auxiliary signal the waveform of which corresponds to the first derivative with respect to time of the waveform of each pulse, a comparator circuit connected to the output of the differentiation circuit to produce as an output signal a pulse whose duration extends from a third instant, defined by the point of zero slope at the peak of the pulse, to a fourth instant, defined by the point in the first auxiliary signal which corresponds with the end of the falling edge of the pulse and where the first auxiliary signal reaches zero level, a counter connected to the output of the comparator circuit to produce as an output signal a pulse the duration of which defines a predetermined time interval starting from the said third instant, and a logical circuit connected to the outputs of the comparator circuit and of the counter and intended to control the following operations:

if the trailing edge of the pulse at the output of the comparator circuit falls within the predetermined time interval, not counting the pulse received at the input of the differentiation circuit and not taking account of the information relating to that pulse, or if the trailing edge of the pulse at the output of the comparator circuit falls outside the predetermined time interval, counting the pulse received at the input of the differentiation circuit as being representative of the passage of a particle through the measuring orifice.

In a preferred version of the methods according to the invention described above a step of the method consists in producing a signal the amplitude of which corresponds to the integral of part of the first auxiliary signal contained between a third instant, defined by the point of zero slope at the peak of the pulse and a fourth instant, defined by the point in the first auxiliary signal which corresponds with the end of the falling edge of the pulse and where the first auxiliary signal reaches zero value.

A preferred version of the devices according to the invention includes an integrator circuit, a first input of which is connected to the output of the differentiation circuit and a second input of which is connected to an output of the logical circuit, to produce an output signal the amplitude of which corresponds to the integral of part of the first auxiliary signal contained between the third instant and the fourth instant.

The methods and the devices according to the invention defined above permit the achievement of a correct amplitude analysis at low cost while accepting a simple fluid flow circuit. Discrimination of particles away from the axis of the counting channel permits the presentation of the distribution of the sizes of particles not contaminated by artifacts while using a relatively short orifice. The rejection of noise pulses is so effective that it permits the use of an orifice of relatively large volume. Typical dimensions for these can be 90 micrometers diameter for a length of 70 micrometers. An orifice with these dimensions guards against inopportune blockages due to the presence of relatively large particles.

By means of integrating the negative part of the first auxiliary signal a signal is obtained whose amplitude corresponds very precisely with the volume of the detected particle. The fact of producing an auxiliary signal corresponding to the first derivative of the pulse received from one of the measuring probes also permits the elimination of a low frequency interference signal which is usually superimposed on the pulse.

BRIEF DESCRIPTION OF THE DRAWINGS

Preferred embodiments of the invention are described hereinafter with reference to the drawings wherein.

DETAILED DESCRIPTION OF THE PREFERRED EMBODIMENTS

Figure 1:
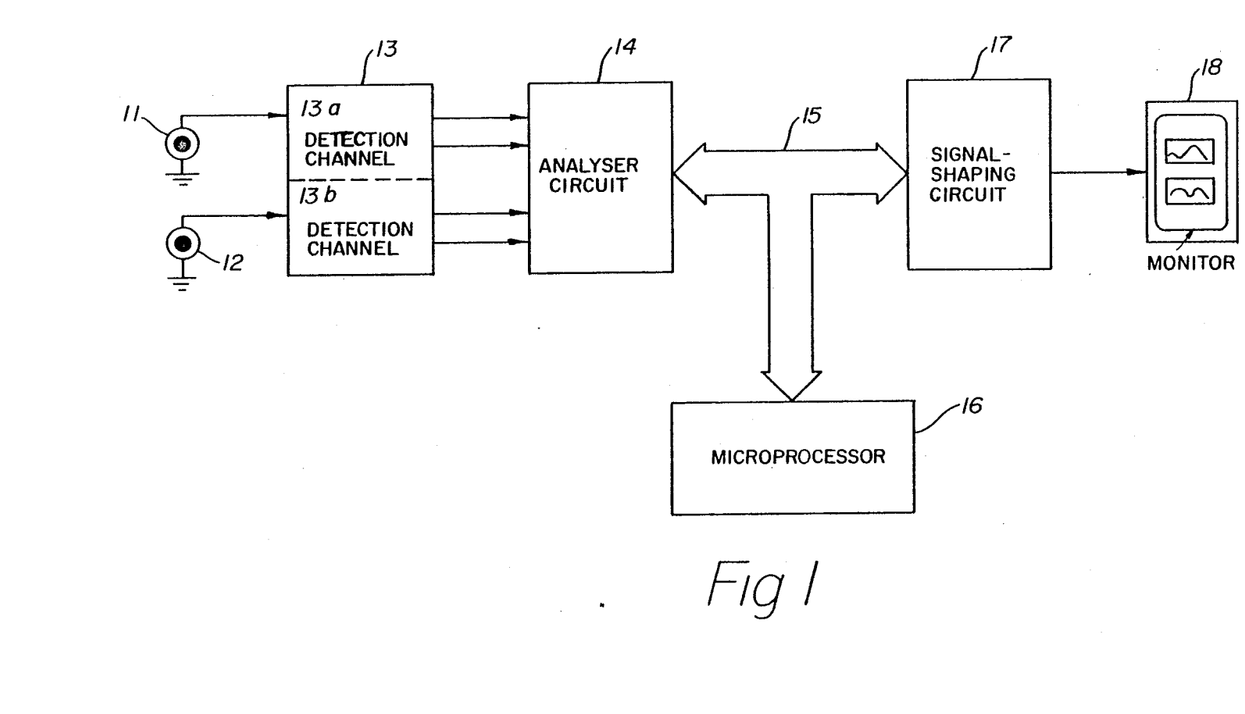
FIG. 1 is a block diagram of the electronic circuits for the acquisition of useful signals and the display of the results obtained in a device for counting blood particles which uses the Coulter detection principle.

The block diagram in FIG. 1 is a diagrammatic representation of a probe 11 for detecting red corpuscles and a probe 12 for detecting white corpuscles. Each of these probes contains a measuring orifice through which a predetermined volume of the liquid sample containing the particles in suspension is passed. With these probes and an associated electrical measuring circuit (which is not shown in the appended Figures) electrical pulses are formed that correspond either with the passage of a blood particle (red or white corpuscle) through the detection orifice of the probe, or with electrical noise. The electrical pulses obtained with each of the probes are applied as an input signal to one of the channels, 13a and 13b respectively, of an electrical detection circuit 13. This circuit checks if each pulse supplied to its input satisfies certain conditions and consequently informs the subsequent system. The outputs of the detection circuit 13 are connected to a multichannel analyser circuit 14 which produces output signals permitting a representation in the form of a histogram to be obtained of the distribution of each type of particle counted according to their amplitudes. The outputs of the analyser circuit are connected by means of an external bus 15 on the one hand to a microprocessor 16, and on the other hand to a signal-shaping circuit 17 for the representation of the said histograms on the screen of a video monitor 18.

The structure and functioning of channels 13a and 13b of the detection circuit 13 are in principle identical. Each of these channels contains means of detecting pulses corresponding with the passage of particles following a trajectory away from the longitudinal axis of the measuring orifice, and preferably also means of detecting electrical noise pulses.

Figure 2:
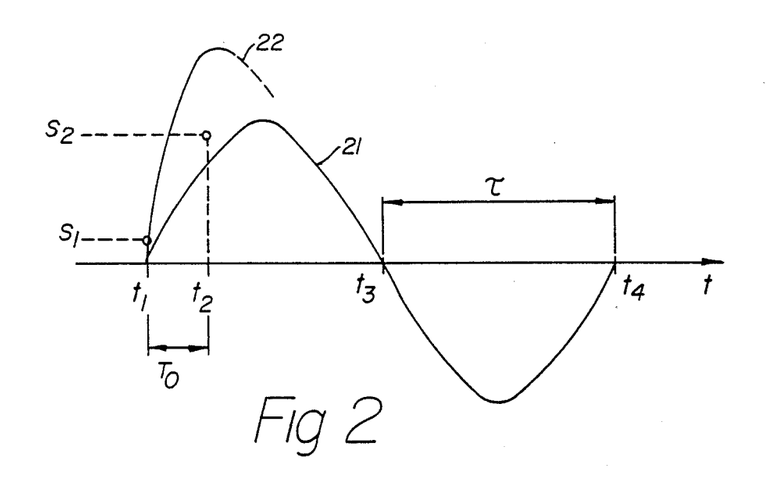
FIG. 2 represents some typical waveforms to illustrate the essential aspects of the methods described below for the selection and production of useful signals.

The principle of the method for the detection of a pulse that corresponds to the passage of a particle following a trajectory away from the longitudinal axis of the measuring orifice is explained below with the help of FIG. 2. This Figure shows a typical waveform 21 of a signal representing the first derivative with respect to time of a pulse which corresponds with the passage of a particle following a trajectory which coincides with the longitudinal axis of the measuring orifice, and a typical waveform 22 of the leading edge of a signal representing the first derivative with respect to time of a pulse which corresponds with the passage of a particle following a trajectory away from the said axis. The method of detection of such a pulse is based on the established fact that the leading edge of its first derivative 22 is steeper than that of the first derivative 21 of a pulse which corresponds with the passage of a particle along the longitudinal axis of the orifice. In order to exploit this difference, the method of detection of pulses which correspond to passages of particles following trajectories away from the axis includes the following steps:

Initially a first auxiliary signal is produced such as 21 or 22 in FIG. 2 of which the waveform corresponds with the first derivative with respect to time of the waveform of each pulse, then a first instant $t_1$ is detected, at which the amplitude of the said first auxiliary signal exceeds a first predetermined threshold level $S_1$. FIG. 2 shows this instant for auxiliary signal 22. It is then checked at a second instant $t_2$, which follows the first instant $t_1$ after a predetermined time interval $T_o$, if the amplitude of the first auxiliary signal at the said second instant has already exceeded a second predetermined threshold level $S_2$, which is chosen to be greater than the first threshold level. If this is the case, as shown in FIG. 2 for the signal 22, the corresponding pulse is considered as a pulse of zero amplitude.

The method described above is preferably associated with the method for the detection of a noise pulse described below with the help of FIG. 2. The method is based on the established fact that the time interval $\tau$ of signal 21 which represents the derivative of a pulse corresponding with the passage of a particle through the orifice is considerably longer than the corresponding period in a signal representing the first derivative of a noise pulse. In order to exploit this difference, the method of detection of noise pulses includes the following steps:

Having produced the first auxiliary signal 21 or 22 in FIG. 2 the waveform of which corresponds with the first derivative with respect to time of the waveform of each pulse, a comparison of the time interval $\tau$ contained between a third instant $t_3$, defined by the point of zero slope at the peak of the pulse, and a fourth instant $t_4$, defined by the point in the first auxiliary signal which corresponds with the end of the falling edge of the pulse and where the first auxiliary signal reaches zero value, is made with a predetermined threshold duration $T_1$. If the measured interval $\tau$ is shorter than the threshold duration $T_1$, the pulse is not counted and the information given by it is not taken into account. In the opposite case, i.e. if the measured interval $\tau$ is equal to or longer than the threshold duration $T_1$, the pulse is considered as representing a particle and the information carried by it is taken into account.

It is interresting to note that each of the two methods that have just been described can be implemented independently. However, their combination is advantageous. Accordingly, an embodiment in which both detection methods are used is described hereinafter.

In order to implement the methods of detection described with reference to FIG. 2 and in order to produce output signals permitting the production of useful output signals, i.e. corresponding with the passage of particles along the longitudinal axis of the measuring orifice, each channel 13a, 13b of the detection circuit 13 in the diagram of FIG. 1 contains the blocks represented in FIG. 3.

Each pulse A supplied by one of the probes 11, 12 is amplified by an amplifier 31. The amplified pulse is applied to the input of a differentiation circuit 32 which produces an output signal B the waveform of which represents the first derivative with respect to time of the waveform of pulse A. This signal B is applied to the inputs of three auxiliary circuits:

an integrator circuit 33, a discriminator circuit 34 to check if pulse A is an electrical noise pulse or if it is a pulse corresponding to the passage of a particle through the measuring orifice, and a discriminator circuit 35 to check if pulse A is a pulse corresponding to the passage of a particle whose trajectory is away from the longitudinal axis of the measuring orifice or it it is a particle whose trajectory coincides with or is very close to the said axis.

According to the result of the checks carried out, the discriminators 34 and 35 supply the subsequent system with the corresponding signals N and G.

In the case of a pulse A which corresponds with the passage of a particle through the measuring orifice, the integrator circuit 33, controlled by a signal M supplied by the discriminator 34, supplies at its output a signal P representing the integral of the negative part of signal B. The amplitude of this signal corresponds very accurately with the volume of the corresponding particle.

Figure 3:
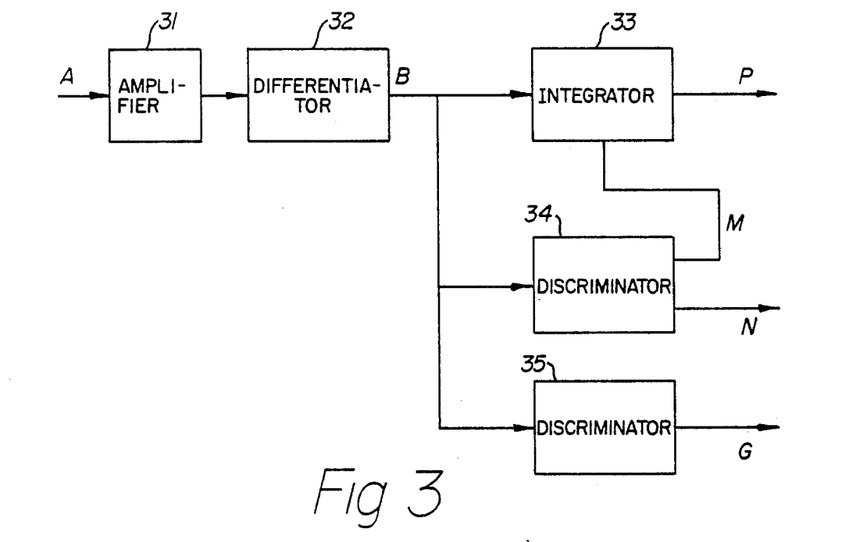
FIG. 3 is a block diagram of the principle circuit of one of the channels 13a, 13b of the detection circuit 13 in FIG. 1.

The structure and functioning of a preferred embodiment of the discriminator circuit 35 in FIG. 3 is described above with the aid of FIGS. 4, 5 and 6.

Figure 4:
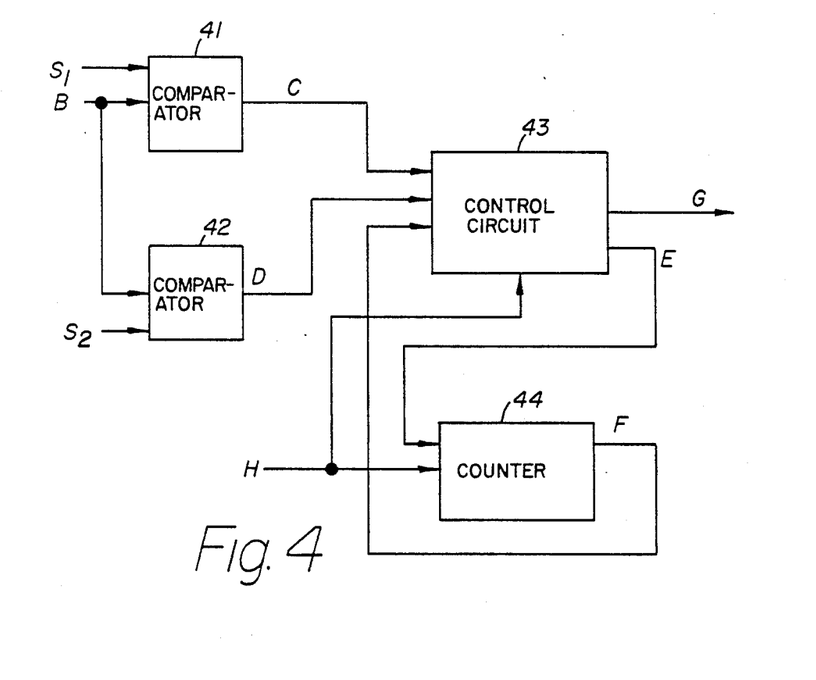
FIG. 4 is a block diagram of the discriminator circuit 35 of FIG. 3.

As shown in the block diagram of the discriminator 35 represented in FIG. 4 the signal B supplied at the output of the differentiation circuit 32 (in FIG. 3) is applied as an input signal to the two comparators 41 and 42. Comparator 41 compares signal B with a first threshold voltage $S_1$, of the order of 100 mV. Comparator 42 compares signal B with a second threshold voltage $S_2$ of the order of 5 V. According to the result of the comparison, each of the comparators 41 and 42 supply a logical output signal, C and D respectively, to an input of a logical control circuit 43. Clock signals H are supplied to an input of the logical circuit 43 and to an input of a counter 44 inserted between an output and an input of the logical circuit 43. Counter 44 is a 4-bit binary counter which makes it possible to define a fixed time interval $T_o$ of the order of 7 $\mu$s, a multiple of the period of the clock signal. Counter 44 is loaded with a precount by a control signal E supplied by the logical circuit 43. At the end of counting, counter 44 supplies a logical signal F representing this event to an input of logical circuit 43.

The discriminator circuit assembly 35 represented in FIG. 4 has, as an output, a logical signal G supplied by the logical control circuit 43; this signal informs the subsequent system of the presence of either a pulse corresponding with the passage of a particle whose trajectory coincides with or is very close to the axis, or a pulse corresponding to a particle having a trajectory out of the axis.

Figure 5:
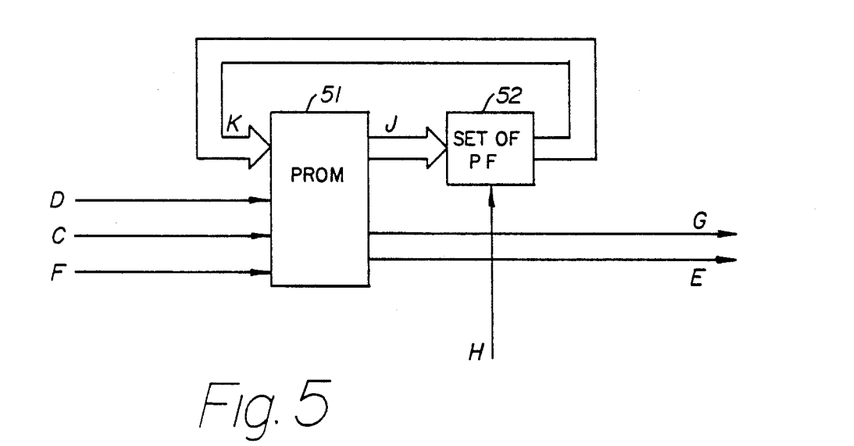
FIG. 5 is a block diagram of a preferred embodiment of the logical circuit 43 in FIG. 4.

FIG. 5 illustrates a preferred embodiment of the logical control circuit 43. This circuit contains a fixed or PROM memory (PROM is an abbreviation of "Programmable Read Only Memory") 51 and a set of bistable flip-flops 52 of SR ("set-reset") type. The memory 51 is programmed such that in conjunction with the set of flip-flops it forms a synchronized sequential system capable of fulfilling the functions of the logical control circuit 43. Memory 51 receives at its inputs on the one hand the logical signals C, D and F coming from comparators 41 and 42 and from counter 44 respectively, and on the other hand a set of signals K corresponding with binary variables used as a storage of the internal states of the system. Memory 51 supplies at its outputs on the one hand the signals G and E which are the output signals of the logical circuit 43, and on the other hand a set of signals J corresponding with binary variables used as a storage of the internal states of the system.

All the flip-flops in the assembly 52 receive the clock signals H. After the active edge of a clock signal has appeared, the set of flip-flops 52 gives output states represented by the set of signals K for the input states represented by the set of signals J.

The functioning of the discriminator circuit represented in FIG. 4 is described below with the help of the waveforms shown in FIG. 6.

Figure 6:
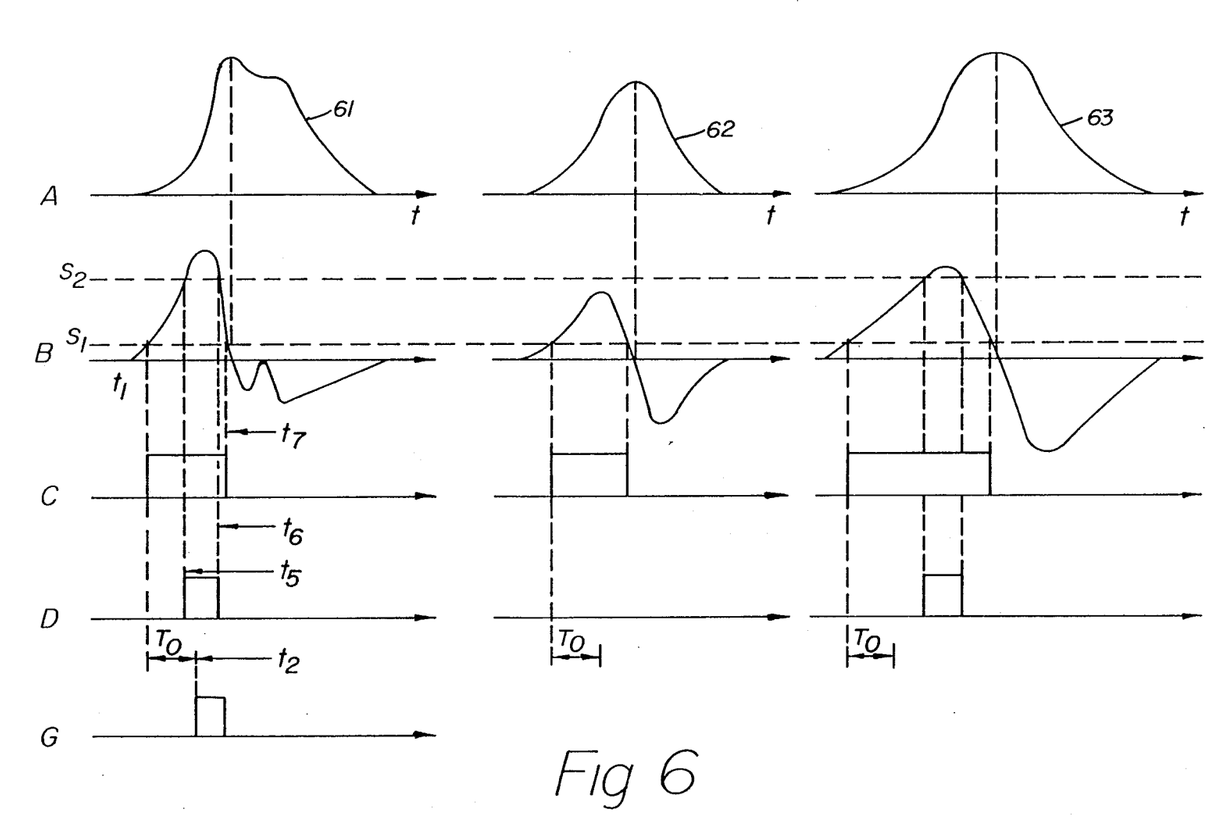
FIG. 6 represents several typical waveforms to illustrate the functioning of the discriminator circuit 35 shown in FIG. 4.

The upper part of FIG. 6 shows three typical waveforms of the pulses A each corresponding to the passage of a particle through the measuring orifice. Waveform 61 corresponds with the passage of a particle away from the axis. Waveform 62 corresponds with the passage of a relatively small particle along the longitudinal axis of the orifice. Waveform 63 corresponds with the passage of a larger particle along the said axis. In the case of waveforms 61 and 63 shown in FIG. 6, the corresponding signals B exceed the second threshold voltage and this gives rise to pulses D at the output of the comparator 42. The beginning and end of each pulse D are determined by the instants $t_5$ and $t_6$ respectively, at which the signal B passes through the second threshold voltage $S_2$. Each pulse D is also applied to an input of the logical control circuit 43. As signal B corresponding to a pulse A having the waveform 62 does not reach the second threshold voltage, this signal does not give rise to a pulse D.

FIG. 6 shows the B and C signals corresponding to each of these waveforms of the pulses A, B appearing at the output of the differentiation circuit 32, and C at the output of the comparator 41. The beginning and end of pulse C are determined by the instants $t_1$ and $t_7$ respectively at which the signal B passes through the first threshold voltage $S_1$. Pulse C is applied to an input of the logical control circuit 43. The leading edge of pulse C defines the instant $t_1$, and triggers in circuit 43 the analysis processes described below for each of the waveforms 61, 62 and 63 of pulses A.

At an instant $t_2 = t_1 + T_o$, $T_o$ being fixed time interval determined by the counting carried out by the counter 44, the logical control circuit 43 checks the presence or absence of a pulse D corresponding with a pulse A received at the input of the differentiation circuit 32. Depending on the waveform of the pulse A this check can give the following results:

For a waveform such as 61 corresponding with the passage of a particle away from the axis, the circuit 43 notes that pulse D is present and then produces at its output a pulse G by means of which circuit 43 informs the subsequent system that pulse A having the waveform 61 must be considered as a pulse of zero amplitude. In this way account is taken of the pulse for a correct counting of the number of particles that pass through the orifice, but waveform 61 is not considered as representing the volume of the particle.

For a waveform such as 62 corresponding to the passage of a relatively small particle along the axis of the orifice, the corresponding signal B does not reach the second threshold $S_2$, resulting in the absence of pulse D. Circuit 43 does not then produce a pulse G and also informs the subsequent system that the waveform 62 is a valid pulse, i.e. a pulse which carries fairly accurate information about the volume of the particle.

For a waveform such as 63 corresponding with the axial passage of a larger particle, signal B exceeds the second threshold $S_2$ and gives rise to a corresponding pulse D, but this pulse appears after the instant $t_2 = t_1 + T_o$. the logical circuit 43 notes this, does not then produce a pulse G and thus informs the subsequent system that waveform 63 is a valid pulse.

The structure and functioning of a preferred embodiment of the discriminator circuit 34 in FIG. 3 is described below with the aid of FIGS. 7, 8 and 9.

Figure 7:
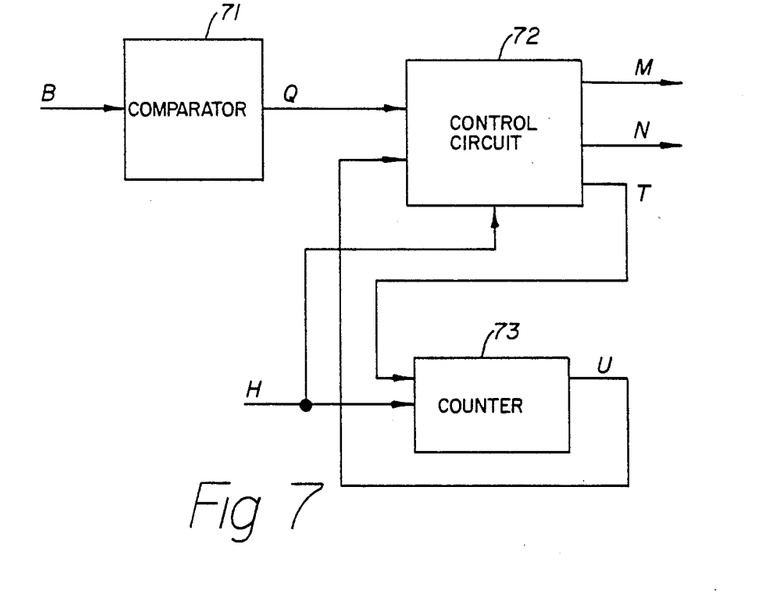
FIG. 7 is a block diagram of the discriminator circuit 34 in FIG. 3.

As shown in the block diagram of the detector 34 represented in FIG. 7, the signal B supplied at the output of the differentiation circuit 32 (in FIG. 3) is applied to an input of a comparator 71 which compares the signal B with a threshold level equal to zero. The logical signal of output Q of this comparator is applied to one of the inputs of a logical control circuit 72. Clock signals H are supplied to an input of logical circuit 72 and to an input of a counter 72 inserted between an output and an input of logical circuit 72. Counter 73 is a 4-bit binary counter which makes it possible to define a fixed time interval $T_1$ of the order of 10 μs, a multiple of the period of the clock signal. The counter 73 is loaded with a precount by a control signal T supplied by logical circuit 72. At the end of the counting, counter 73 supplies a logical signal U representing this event to an input of logical circuit 72.

The discriminator circuit 34 respresented in FIG. 7 has as outputs on the one hand the control signal M supplied by the logical circuit 72 to an input of the integrator 33 (in FIG. 3) and, on the other hand, a logical signal N supplied by logical circuit 72; if necessary, this signal informs the subsequent system either of the presence of an analog signal P which corresponds with a valid pulse, which is representative of the volume of the particle corresponding with the said pulse, and which is ready to be considered for analysis, or of the presence of a noise pulse.

Figure 8:
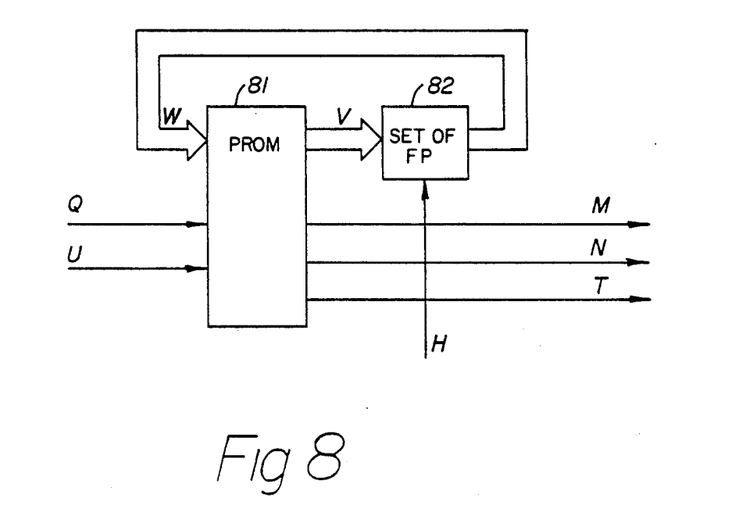
FIG. 8 is a block diagram of a preferred embodiment of the logical circuit 72 in FIG. 7.

FIG. 8 illustrates a preferred embodiment of the logical control circuit 72. This circuit contains a fixed or PROM memory 81 and a set of SR type bistable flip-flops 82. The memory 81 is programmed such that in conjunction with the set of flip-flops it forms a synchronized sequential system capable of fulfilling the functions of the logical control circuit 72. Memory 81 receives as input signals on the one hand the logical signals Q and U coming from comparator 71 and counter 73 respectively, and on the other hand set of signals W corresponding with binary variables used as a storage of the internal states of the system.

Memory 81 supplies at its outputs on the one hand the signals M, N and T, which are the output signals of logical circuit 72, and on the other hand a set of signals V corresponding with binary variables used as a storage of the internal states of the system.

All the flip-flops in the assembly 82 receive the clock signals H. After the active edge of a clock signal has appeared, the set of flip-flops 82 gives the output states represented by the set of signals W for the input states represented by the set of signals V.

The configurations of the logical control circuits 43 and 72 described above with reference to FIGS. 5 and 8 respectively are advantageous, since with fairly simple structures they offer a sufficient operational flexibility.

The functioning of the discriminator circuit 34 represented in FIG. 7 is described below with the help of the waveforms shown in FIG. 9.

Figure 9:
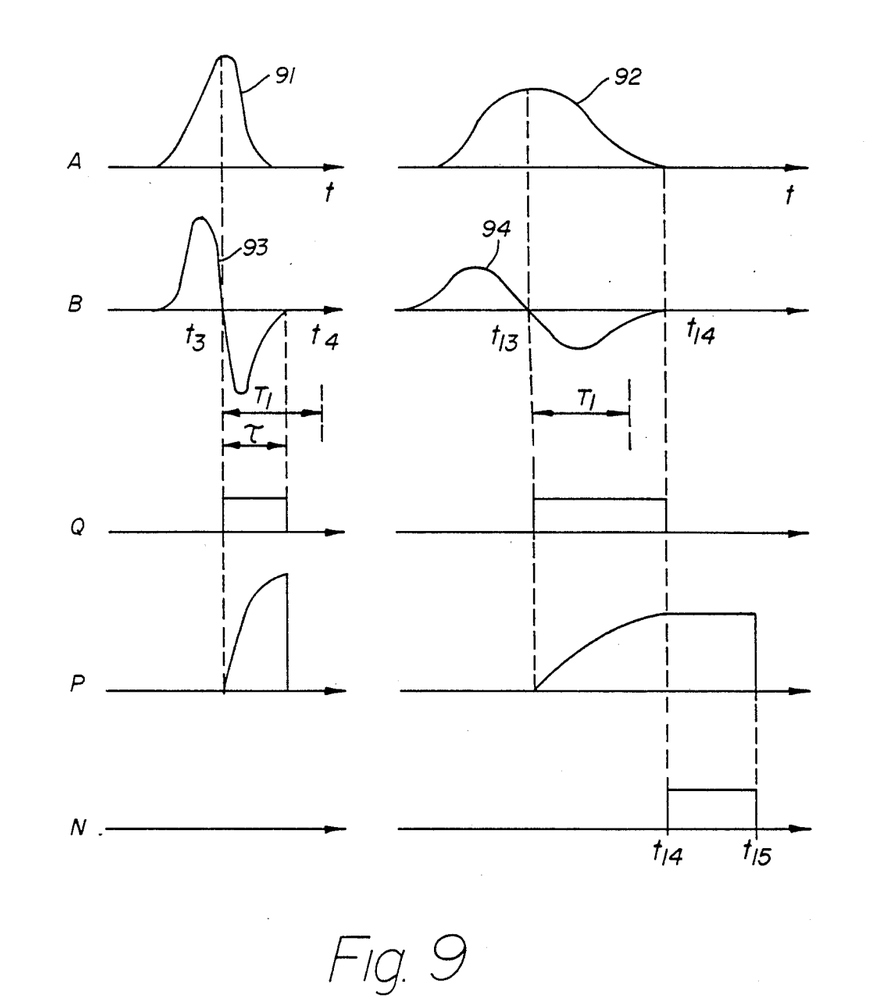
FIG. 9 represents several typical waveforms to illustrate the functioning of the discriminator circuit in FIG. 7.

The upper part of FIG. 9 shows two different waveforms of the pulses A at the input of differentiator 32 in FIG. 3. Pulse 91 is an electrical noise pulse. Pulse 92 corresponds with the passage of a particle through the measuring orifice.

For a noise pulse such as 91 the differentiator 32 generates a signal B having the waveform 93, and the comparator 71 produces a corresponding pulse Q having the same duration as the negative part of signal B and lasting from instant $t_3$ to instant $t_4$. From $t_3$ to $t_4$ the logical circuit 72 supplies the control signal M to the integrator 33 thus authorizing the integration of signal B over this period. At instant $t_3$ the logical circuit 72 initiates the time counting by counter 73 by means of control signal T. At instant $t_4$ corresponding with the end of pulse Q for the signal 93, the logical circuit 72 notes that counter 73 has not yet finished its counting cycle of duration $T_1$ and then rejects pulse 91 by the absence of a signal N at its output indicating a valid pulse, resets integrator 33 and counter 73 to zero and is thus ready to process a new pulse.

For an input pulse such as 92 the differentiator 32 generates a signal B having the waveform 94, and the comparator 71 produces a corresponding pulse Q, and between instants $t_{13}$ and $t_{14}$ the discriminator circuit in FIG. 7 carries out the same operations as between $t_3$ and $t_4$. This time the logical circuit 72 nots that at instant $t_{14}$ the counter 73 has already completed its counting cycle of duration $T_1$, and supplies at its output a logical signal N indicating that waveform 94 corresponds with a valid pulse A and thus informs the subsequent system that at the output of integrator 33 a valid analog signal P is ready to be analyzed. After a time interval going from instant $t_{14}$ to instant $t_{15}$, during which the subsequent system has time to process signal P, the integrator 61 is reset to zero. At instant $t_{15}$ the discriminator circuit in FIG. 7 is reinitialized and is again ready to process a new signal B arriving at its input.

Figure 10:
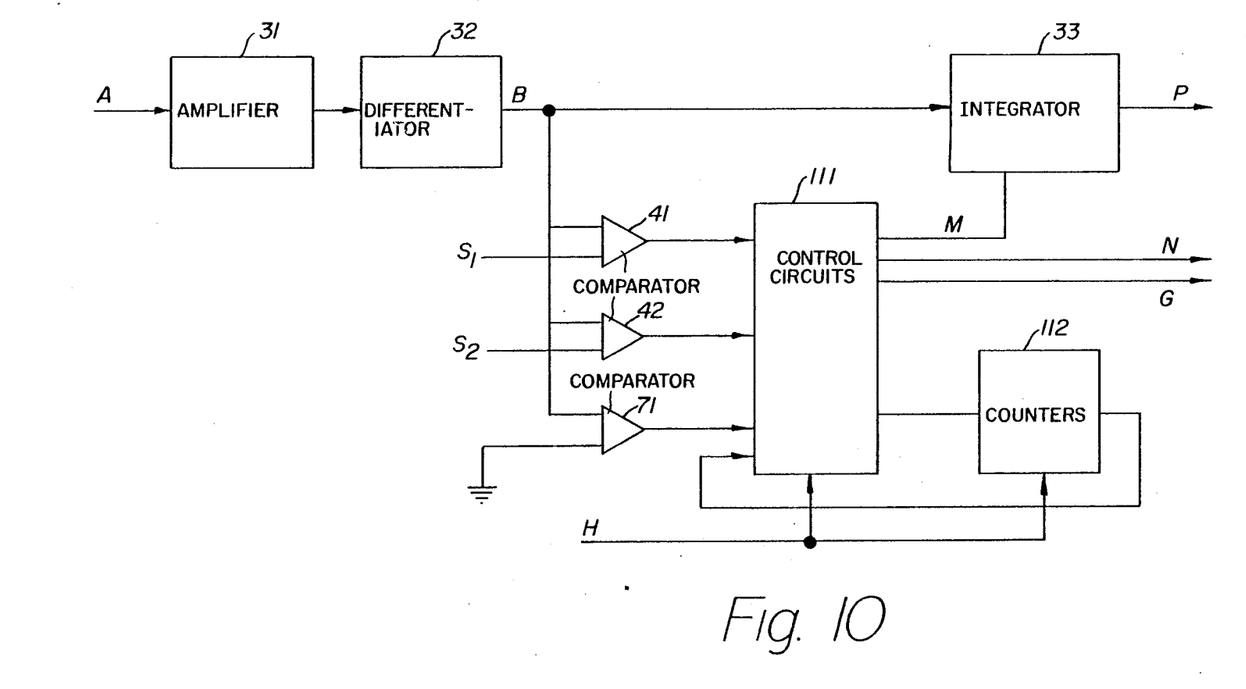
FIG. 10 is a block diagram obtained by combining the block diagrams shown in FIGS. 3, 4 and 7.

FIG. 10 shows a block diagram of one channel 13a or 13b of the detection circuit 13 in FIG. 1 containing all the blocks necessary for detecting pulses corresponding with the passage of particles whose trajectories are away from the longitudinal axis of the orifice, and for the rejection of noise pulses. As can be appreciated this diagram corresponds with a combination of the blocks shown in FIGS. 3, 4 and 7. In the diagram of FIG. 10, block 111 contains the logical control blocks 43 and 72 shown in FIGS. 4 and 7 respectively. Similarly block 112 in FIG. 10 contains counters 44 and 73 in FIGS. 4 and 7 respectively.

As an example it can be said that the following magnitudes give good results in the counting of red corpuscles:

(a) HYDRODYNAMIC MAGNITUDES
  volume of liquid analyzed: 400 μl
  red corpuscles dilution factor: 50,000
  pressure difference across the orifice: 200 mbars
With these values, the counting time is of the order of 12 seconds.

(b) ELECTRICAL MAGNITUDES
  voltage applied to the electrodes placed on either side of the measuring orifice: 40 volts.
  voltage gain of amplifier 31 (see FIGS. 3 and 10): 4,000
  $S_1 = 100$ mvolts
  $S_2 = 5$ volts The values of $S_1$ and $S_2$ are proportional to the internal volume of the device's measuring orifice.

(c) TIME MAGNITUDES
  $T_o = 7$ μs
  $T_1 = 10$ μs

The values $T_o$ and $T_1$ are inversely proportional to the speed at which the particles pass through the device's measuring orifice. The values indicated above are valid for a measuring orifice having a diameter of 90 μm and a length of 70 μm, and for a pressure difference of 200 mbars across the said orifice.

We claim:

1. A method for the analysis of particles in suspension in a fluid having a conductivity different from that of the particles, comprising:
   (a) passing the fluid through an orifice;
   (b) applying an electronic signal across the orifice;
   (c) producing a plurality of electrical pulses (A) corresponding to the changes in the signal level caused by the passage of particles through the orifice;
   (d) producing a first auxiliary signal (B) the waveform of which corresponds to the first derivative with respect to time of the waveform of each pulse (A);
   (e) detecting a first instant ($t_1$) at which the amplitude of the first auxiliary signal exceeds a predetermined first threshold level ($S_1$);
   (f) determining at a second instant ($t_2$), which follows at a predetermined time interval (To) after the first instant ($t_1$), whether the amplitude of the first auxiliary signal at the said second instant has exceeded a second predetermined threshold level ($S_2$), which is greater than the first threshold level; and
   (g) if the said amplitude has exceeded the second threshold level ($S_2$), considering the pulse as a pulse (A) of zero amplitude.

2. A method for the analysis of particles in suspension in a fluid having a conductivity different from that of the particles, comprising:
   (a) passing the fluid through an orifice;
   (b) applying an electronic signal across the orifice;
   (c) producing a plurality of electrical pulses (A) corresponding to the changes in the signal level caused by the passage of particles through the orifice;
   (d) producing a first auxiliary signal (B) the waveform of which corresponds to the first derivative with respect to time of the waveform of each pulse (A);
   (e) comparing the time interval ($\tau$) between a third instant ($t_3$), defined by the point of zero slope at the peak of the pulse, and a fourth instant ($t_4$), defined by the point in the first auxiliary signal which corresponds with the end of the falling edge of the pulse and where the first auxiliary signal reaches zero value, with a predetermined threshold duration ($T_1$);
   (f) if the measured interval ($\tau$) is shorter than the threshold duration ($T_1$), not counting the pulse and not taking the information given by that pulse into consideration; and
   (g) if the measured interval ($\tau$) is equal to or longer than the threshold duration ($T_1$), considering the pulse as being representative of a particle and taking account of the information given by that pulse.

3. A method according to claims 1 or 2, wherein a step of the method consists in producing a signal the amplitude of which corresponds to the integral of part of the first auxiliary signal contained between a third instant ($t_3$), defined by the point of zero slope at the peak of the pulse and a fourth instant ($t_4$), defined by the point in the first auxiliary signal which corresponds with the end of the falling edge of the pulse and where the first auxiliary signal reaches zero value.

4. A device for analyzing particles in suspension in a fluid having a conductivity different from that of the particles, said device having a pulse detector which includes the following circuits:
   (a) a differentiation circuit to produce a first auxiliary signal the waveform of which corresponds to the first derivative with respect to time of the waveform of each pulse;
   (b) a first comparator connected to the output of the differentiation circuit to detect a first instant ($t_1$) at which the first auxiliary signal exceeds a predetermined first threshold level ($S_1$), and to supply a corresponding output signal;
   (c) a counter connected to the output of the first comparator to produce as an output signal a pulse the duration of which defines a predetermined time interval (To) starting from the said first instant ($t_1$);
   (d) a second comparator connected to the output of the differentiation circuit to detect a second instant ($t_2$) at which the first auxiliary signal exceeds a second predetermined threshold level ($S_2$), which is larger than the first threshold level ($S_1$), and to provide a corresponding output signal; and
   (e) a logical circuit connected to the outputs of the first and second comparators and of the counter, and intended to control the consideration of pulses received at the input of the differentiation circuit as pulses of zero amplitude if the second instant ($t_2$) falls within the time interval ($T_0$) defined by the counter.

5. A device for analyzing particles in suspension in a fluid having a conductivity different from that of the particles, said device having a pulse detector which includes the following circuits:
(a) a differentiation circuit to produce a first auxiliary signal the waveform of which corresponds to the first derivative with respect to time of the waveform of each pulse,
(b) a comparator circuit connected to the output of the differentiation circuit to produce as an output signal a pulse whose duration ($\tau$) extends from a third instant ($t_3$), defined by the point of zero slope at the peak of the pulse to a fourth instant ($t_4$), defined by the point in the first auxiliary signal which corresponds with the end of the falling edge of the pulse and where the first auxiliary signal reaches zero level;
(c) a counter connected to the output of the comparator circuit to produce as an output signal a pulse the duration of which defines a predetermined time interval ($T_1$) starting from the said third instant ($t_3$); and
(d) a logical circuit connected to the outputs of the comparator circuit and of the counter and controlling the following operation:
  (i) if the trailing edge of the pulse at the output of the comparator circuit falls within the predetermined time interval ($T_1$), not counting the pulse received at the input of the differentiation circuit and not taking account of the information relating to that pulse; and
  (ii) if the trailing edge of the pulse at the output of the comparator circuit falls outside the predetermined time interval ($T_1$), counting the pulse received at the input of the differentiation circuit as being representative of a particle.

6. The device according to claim 5, further comprising an integrator circuit a first input of which is connected to the output of the differentiation circuit and a second input of which is connected to an output of the logical circuit, to produce an output signal the amplitude of which corresponds to the integral of part of the first auxiliary signal contained between the third instant and the fourth instant.

* * * * *